United States Patent [19]

Reber et al.

[11] Patent Number: 5,948,694
[45] Date of Patent: Sep. 7, 1999

[54] MOLECULAR DETECTION APPARATUS

[75] Inventors: William L. Reber, Schaumburg, Ill.; Michael K. Stenstrom, Los Angeles, Calif.; Cary D. Perttunen, Shelby Township, Mich.

[73] Assignee: Motorola, Inc., Schaumburg, Ill.

[21] Appl. No.: 08/838,491

[22] Filed: Apr. 7, 1997

[51] Int. Cl.$^6$ .......................... G01N 33/543; G01N 1/14; G01N 21/00; G01N 21/29

[52] U.S. Cl. .......................... 436/518; 436/805; 436/810; 422/50; 422/55; 422/56; 422/58; 422/82.05; 422/310

[58] Field of Search .................................... 436/518, 805, 436/810; 422/50, 56, 58, 82.05, 310; 210/493.5; 435/278.1, 810

[56] References Cited

U.S. PATENT DOCUMENTS

| | | | |
|---|---|---|---|
| 2,925,171 | 2/1960 | Eaton . | |
| 4,720,455 | 1/1988 | Babu et al. | 435/7 |
| 5,001,048 | 3/1991 | Taylor et al. | 435/4 |
| 5,122,452 | 6/1992 | Yamazaki et al. | 435/7.92 |
| 5,268,305 | 12/1993 | Ribi et al. | 436/501 |
| 5,573,921 | 11/1996 | Behnke et al. | 435/7.92 |
| 5,656,503 | 8/1997 | May et al. | 436/514 |

OTHER PUBLICATIONS

"Berkeley Lab Invents Instant E. Coli Test", New Technology Week, Dec. 16, 1996, p. 10.

"Direct Colorimetric Detection of a Receptor–Ligand Interaction by a Polymerized Bilayer assembly", Deborah H. Charych, Jon O. Nagy, Wayne Spevak, & Mark D. bednarski; Science, vol. 261, Ju. 30, 1993, pp. 585–588.

"Polydiacetylene Liposomes Functionalized with Sialic Acid Bind and Colorimetrically Detect Influenza Virus", Anke Reichert, Jon O. Nagy, Spevak, & Deborah Charych; J. Am. Chem. Soc. 1995, 117, 829–830.

"A 'litmus test' for molecular recognition using artificial membranes", Deborah Charych, Quan Cheng, Anke Reichert, Geroffrey Kuziemko, Mark Stroh, Jon O. Nagy, Wayne Spevak, & Raymond C. Stevens; Chemistry & Biology, Feb. 1996; 3:113–120.

"Direct Flu Detection and Potential Therapeutics", Ernest Orlando Lawrence Berkeley National Laboratory.

"New Sensor Provide First Instant Test for Toxic E. Coli Organism", Jeffery Kahn, Berkeley Lab Research News, Dec. 10, 1996, pp. 1–3.

Charych et al. Mater. Res. Soc. Symp. Proc. 292: 153–161 (B), 1993.

Kramer. J. AOAC International 79: 1245–1254, 1996.

Spevak et al. Adv. Mater. 7 (1): 85–89, 1995.

Pan et al. Langmuir 13: 1365–1367, Mar. 1997.

Taylor et al. In: Protein Immobilization Fundamentals and Applications. (Ed)RFTaylor, Chapter 8, pp. 263–303, 1991.

*Primary Examiner*—James C. Housel
*Assistant Examiner*—S. Devi
*Attorney, Agent, or Firm*—Jeffrey G. Toler; James E. Gauger

[57] ABSTRACT

A molecular detection apparatus comprises a molecular receptor (20), a detection element (22) responsive to the molecular receptor (20), and a substrate (24) which supports the detection element (22). The molecular detection apparatus further includes a grasping member (26) and an elongated member (30) to couple the grasping member (26) to the substrate (24).

9 Claims, 4 Drawing Sheets

MOLECULAR DETECTION APPARATUS

TECHNICAL FIELD

The present invention relates to molecular detection devices.

BACKGROUND OF THE INVENTION

Lawrence Berkeley National Laboratory has announced and published methods and systems for direct colorimetric detection of receptor-ligand interaction using a polymerized bilayer sensor. The sensor comprises a plurality of sensor molecules fabricated into a thin film. Each sensor molecule includes a molecular receptor which binds to a molecule of interest, such as *E. coli* 0157:H7. The backbone of the sensor molecule includes a colorimetric detection element in the form of a long diacetylene lipid. Exposure to ultraviolet light links the molecular receptor with the colorimetric detection element by activating a triple bond within the diacetylene lipids. A blue-tinted polydiacetylene (PDA) film results from this step.

The PDA film is sensitive to changes on its surface as manifested by the wavelength of light transmitted thereby. For example, when *E. coli* 0157:H7 toxins bind to the surface of the sensor, the backbone chain of PDA reorganizes to produce a red tint. The colorimetric reaction from blue to red is visible by a naked eye.

In another application, a synthetic membrane based on polydiacetylenes is formed to have influenza virus binding sites on its surface. The color of the membrane changes from blue to red in response to a binding event of a sample of influenza virus to the binding sites.

BRIEF DESCRIPTION OF THE DRAWINGS

The invention is pointed out with particularity in the appended claims. However, other features of the invention may become more by referring to the following detailed description in conjunction with the accompanying drawings in which:

DETAILED DESCRIPTION OF A PREFERRED EMBODIMENT

Figure 1:
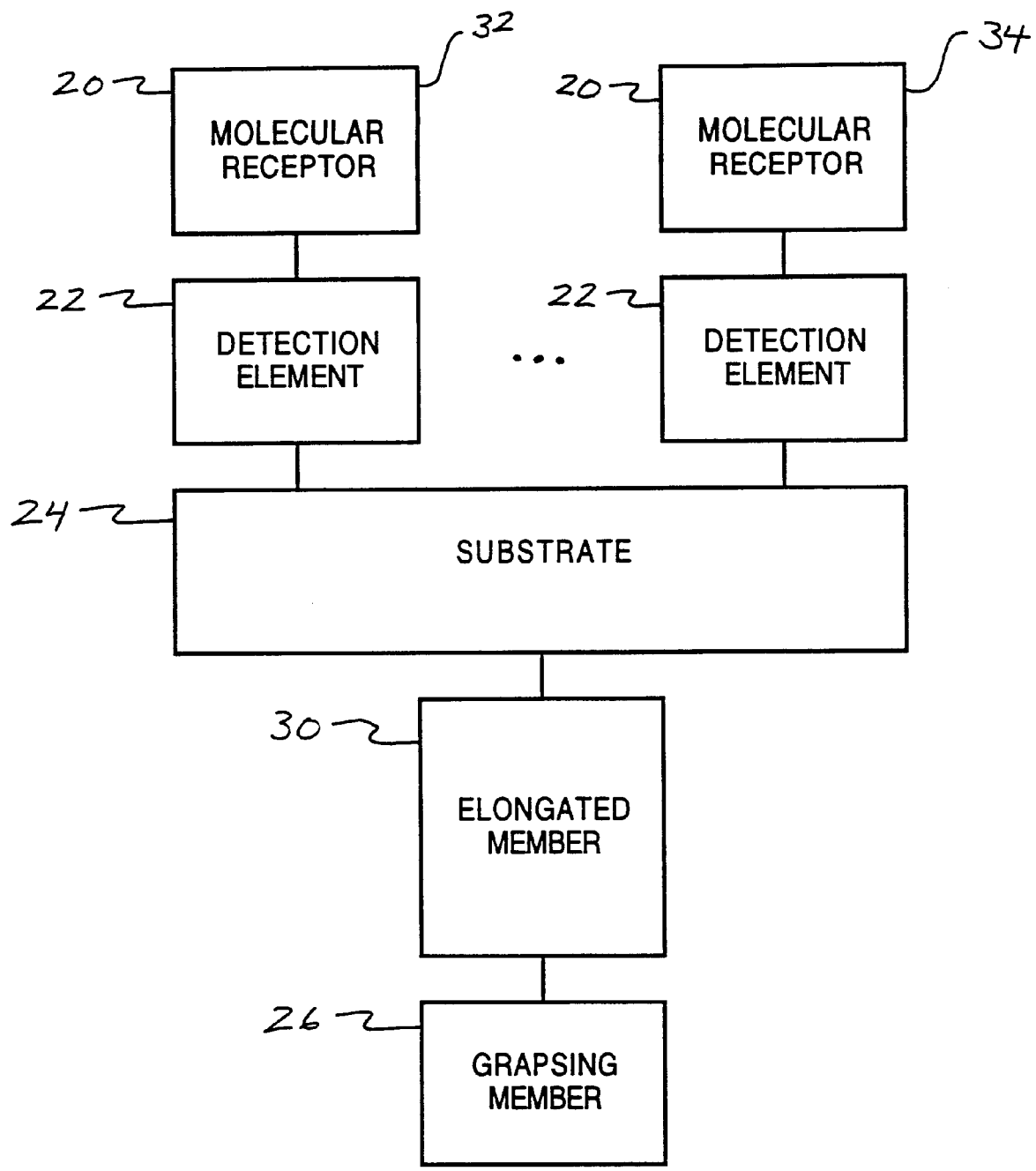
FIG. 1 is a block diagram of a molecular detection apparatus in accordance with the present invention.

FIG. 1 is a block diagram of a molecular detection apparatus in accordance with the present invention. The molecular detection apparatus includes at least one molecular receptor 20 specific to at least one molecule which is to be detected. Examples of types of molecules which can be detected include, but are not limited to: polynucleotides such as DNA strands and RNA strands; pathogens such as coliforms, viruses, bacteria, *E. coli*, malaria, and parasites; proteins; and enzymes. The at least one molecular receptor 20 can include at least one ligand specific to a desired molecule to be detected.

The molecular detection apparatus further includes at least one detection element 22 responsive to the at least one molecular receptor 20. Each detection element 22 provides an indication of a molecular recognition event from its respective molecular receptor 20. In a preferred embodiment, each detection element 22 includes a visual detection element which produces a visual indication in response to a binding event between the molecular receptor 20 and a molecule. The visual indication allows an individual to determine the existence of the molecule by visually inspecting the detection element 22.

In a preferred embodiment, each detection element 22 includes a colorimetric detection element which changes color in response to a molecular recognition event. The colorimetric detection element can exhibit a first color such as blue when the molecular receptor is absent of a molecule bound thereto, and can exhibit a second color such as red when a molecule is bound to the molecular receptor. The colorimetric detection element can include a diacetylene lipid as described earlier.

The molecular detection apparatus further includes a substrate 24 which supports the detection element 22 and the molecular receptor 20. The substrate 24 can have a variety of forms, and can be formed using a variety of materials. Examples of materials from which the substrate 24 is formed include, but are not limited to, paper, plastic, and glass. Examples of forms of the substrate 24 include, but are not limited to, a planar form, a non-planar form, a cylindrical form, a hollowed form, and a bead form.

Preferably, the substrate 24 has a surface which promotes adsorption. The substrate 24 can be formed of an adsorptive material, or the surface can be coated with an adsorptive material. The adsorptive material is beneficial in capturing molecules, such as viruses, at the surface of the substrate 24. Optionally, the surface of the substrate 24 can be charged to attract oppositely-charged molecules thereto.

The substrate 24 can be formed using an organic polymer whose charge, molecular weight, and length is managed. The organic polymer can be manufactured to be food grade in order to be consumable.

The at least one molecular receptor 20 and the at least one detection element 22 can have the form of a film disposed on a surface of the substrate 24. For example, the at least one molecular receptor 20 and the at least one detection element 22 can be included in a PDA film as described earlier. A monolayer support can be interposed between the substrate 24 and the detection element 22.

The at least one molecular receptor 20 and the at least one detection element 22 can be patterned on the substrate 24 to form an image viewable when molecules bind to the at least one molecular receptor 20. Optionally, the substrate 24 has a background color, such as blue, similar to the first color of the at least one detection element 22 when bound molecules are absent from the at least one molecular receptor 20. In this case, the pattern of the at least one detection element 22 is substantially unnoticeable in the absence of molecules bound thereto. The pattern of the at least one molecular receptor 20 becomes apparent as its color changes in response to molecules binding thereto. The pattern of the image can include an icon, textual information, and/or graphical information indicative of a condition of detecting the molecules.

A grasping member 26 allows an individual to grasp the molecular detection apparatus. The grasping member 26 can include a container cap, a tag, a tab, a handle, a rod, or a stick which can be grasped by a hand of the individual.

The molecular detection apparatus further includes an elongated member 30 which couples the grasping member 26 to the substrate 24. The elongated member 30 has a length dimension greater than each of its width dimensions. Examples of the elongated member 30 include, but are not limited to: a flexible line such as a string, a cord, a thread, or a wire; and a rigid, semi-rigid, or resilient member such as a rod, a stick, or a tube. The elongated member 30 can be formed of a variety of materials, including but not limited to, paper, plastic, metal, and fabric. The elongated member 30 can be solid, hollow, or stranded. Further, the elongated member 30 can be either telescoping or otherwise extendible to have a smaller footprint in storage.

At a position along the length dimension, the elongated member 30 can be partitioned into a first half and a second half, wherein the grasping member 26 is coupled at the first half and the substrate 24 is coupled at the second half. Further, the grasping member 26 can be coupled at or near a first end of the elongated member 30. Similarly, the substrate 24 can be coupled at or near a second end of the elongated member 30.

In some embodiments, the grasping member 26 and the elongated member 30 are provided by a unitary member. For example, a single stick can provide both the grasping member 26 and the elongated member 30. Similarly, the elongated member 30 and the substrate 24 can be provided by a unitary member. Here, for example, a single stick can provide both the elongated member 30 and the substrate 24 to support the detection element 22.

It is noted that the at least one molecular receptor 20 can include a first molecular receptor 32 for detecting a first molecule and a second molecular receptor 34 for detecting a second molecule, where the first molecule differs from the second molecule. In general, the at least one molecular receptor 20 can include a plurality of different molecular receptors.

Figure 2:
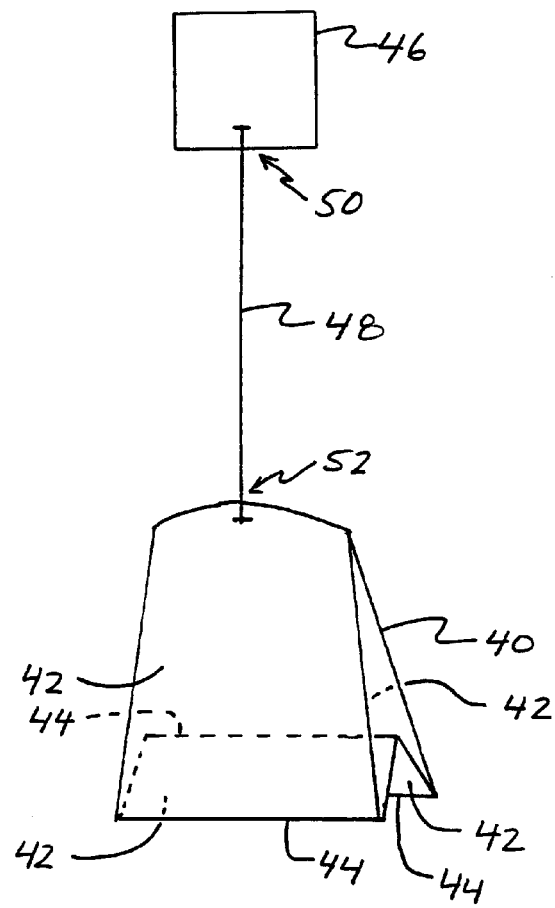
FIG. 2 illustrates a first embodiment of a molecular detection apparatus in accordance with the present invention.

FIG. 2 illustrates a first embodiment of a molecular detection apparatus in accordance with the present invention. The molecular detection apparatus includes a substrate 40 which supports a film of at least one detection element and at least one molecular receptor. The at least one detection element and the at least one molecular receptor are coated onto at least one surface 42 of the substrate 40. The substrate 40 can include at least one fold 44 to provide a greater surface area for supporting detection elements and molecular receptors. As illustrated, the at least one fold 44 can include a plurality of concertina folds.

The substrate 40 can be formed of paper, plastic, or an organic polymer, for example. Optionally, the substrate 40 is formed of a permeable material which allows a fluid to flow therethrough. The permeable material can include either a porous material or a perforated material to allow a fluid, such as a liquid or a gas, to flow therethrough.

The molecular detection apparatus includes a grasping member in the form of a tag 46. The tag 46 can be formed of a sheet of material such as paper or plastic. Although illustrated to have the shape of a square, the tag 46 can have any shape in general.

An elongated member having the form of a flexible line 48 couples the tag 46 to the substrate 40. The flexible line 48 can be formed of thread, string, wire, or any thin cord. The flexible line 48 includes a first end 50 and a second end 52. The tag 46 is coupled to the flexible line 48 near the first end 50. The substrate 40 is coupled to the flexible line 48 near the second end 52.

The flexible line 48 can be coupled to the tag 46 and the substrate 40 in a variety of ways. The flexible line 48 can be tied to either or both of the tag 46 and the substrate 40. Alternatively, the flexible line 48 can be adhered to either or both of the tag 46 and the substrate 40. As another alternative, the flexible line 48 can be fastened to either or both of the tag 46 and the substrate 40 using a fastener such as a staple.

Figure 3:
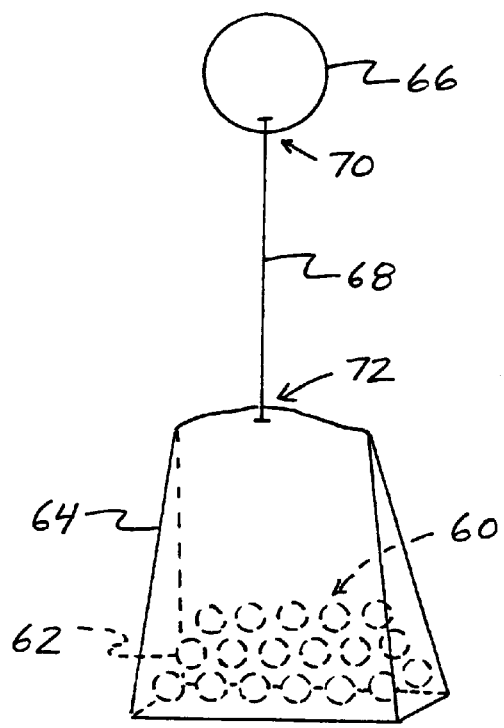
FIG. 3 illustrates a second embodiment of a molecular detection apparatus in accordance with the present invention.

FIG. 3 illustrates a second embodiment of a molecular detection apparatus in accordance with the present invention. The molecular detection apparatus includes a plurality of substrates 60 each supporting at least one detection element and at least one molecular receptor. Each of the substrates 60 has the form of bead 62. The at least one detection element and the at least one molecular receptor are coated onto an external surface of each bead 62. Each bead 62 can be formed of plastic or an organic polymer, for example.

The molecular detection apparatus includes a container 64 which contains the substrates 60. Preferably, the container 64 includes a permeable portion to allow fluid to flow therethrough while simultaneously retaining the substrates 60 therein. The container 64 can be formed of a porous sheet of material such as filter paper or another filter medium. Alternatively, the container 64 can be formed of a perforated sheet of material having openings sized smaller than the substrates 60.

The molecular detection apparatus includes a grasping member in the form of a tag 66. The tag 66 can be formed of a sheet of material such as paper or plastic. Although illustrated to have the shape of a circle, the tag 66 can have any shape in general.

An elongated member having the form of a flexible line 68 couples the tag 66 to the substrates 60 via the container 64. The flexible line 68 can be formed of thread, string, wire, or any thin cord. The flexible line 68 includes a first end 70 and a second end 72. The tag 66 is coupled to the flexible line 68 near the first end 70. The container 64 is coupled to the flexible line 68 near the second end 72.

The flexible line 68 can be coupled to the tag 66 and the container 64 in a variety of ways. The flexible line 68 can be tied to either or both of the tag 66 and the container 64. Alternatively, the flexible line 68 can be adhered to either or both of the tag 66 and the container 64. As another alternative, the flexible line 68 can be fastened to either or both of the tag 66 and the container 64 using a fastener such as a staple.

Figure 4:
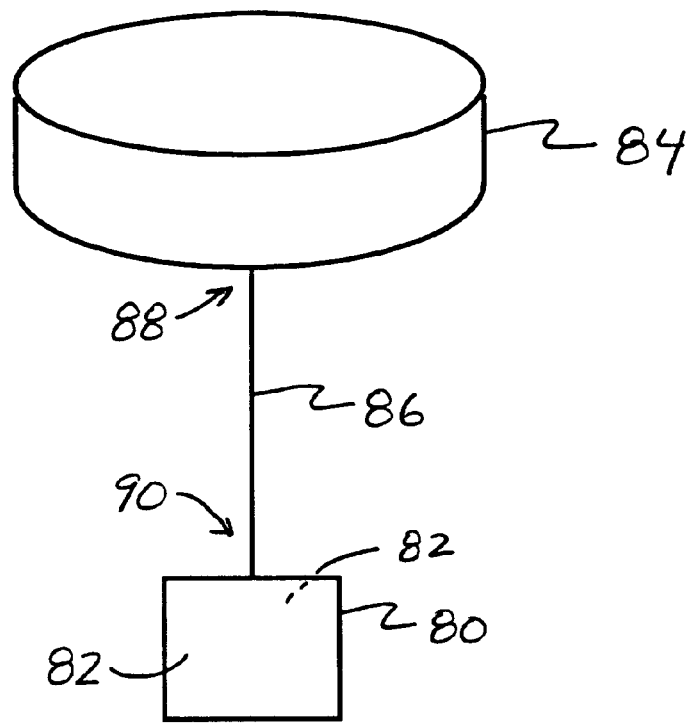
FIG. 4 illustrates a third embodiment of a molecular detection apparatus in accordance with the present invention.

FIG. 4 illustrates a third embodiment of a molecular detection apparatus in accordance with the present invention. The molecular detection apparatus includes a substrate 80 which supports a film of at least one detection element and at least one molecular receptor. The at least one detection element and the at least one molecular receptor are coated onto at least one surface 82 of the substrate 80.

The molecular detection apparatus includes a grasping member in the form of a container cap 84. The container cap 84 can have the form of a cap, a lid, or a cover for a container such as a bottle, a jar, or a can.

An elongated member 86 couples the container cap 84 to the substrate 80. The elongated member 86 can be formed of a flexible line, a semi-rigid line, or a rigid line. In preferred embodiments, the elongated member 86 is formed of either a thread, a string, a wire, a thin cord, or a plastic rod or stick. Optionally, at least one detection element and at least one molecular receptor are coated onto an external surface of the elongated member 86.

The container cap 84 is coupled at or near a first end 88 of the elongated member 86. The substrate 80 is coupled at or near a second end 90 of the elongated member 86. The elongated member 86 can be tied, adhered, or fastened to either or both of the container cap 84 and the substrate 80.

Figure 5:
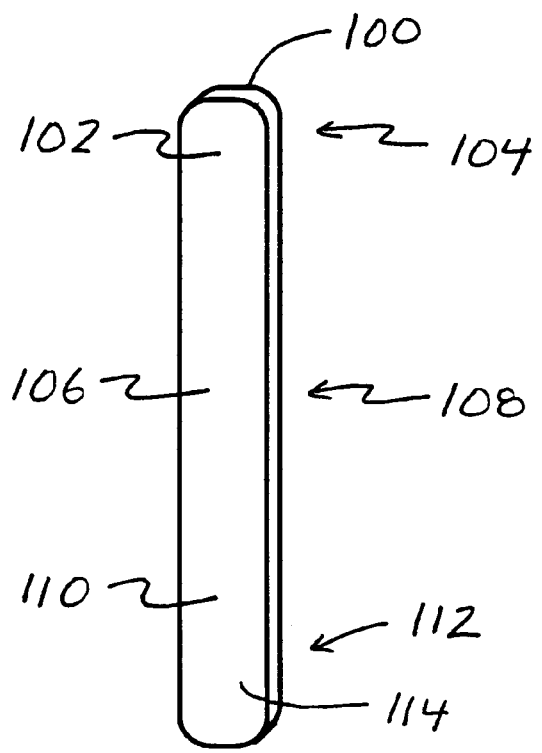
FIG. 5 illustrates a fourth embodiment of a molecular detection apparatus in accordance with the present invention.

FIG. 5 illustrates a fourth embodiment of a molecular detection apparatus in accordance with the present invention. The molecular detection apparatus includes a unitary member having the form of a stick 100. The stick 100 can be formed of materials including but not limited to paper, plastic, wood, and glass. The stick 100 can be either solid or hollowed.

The stick 100 provides a grasping member 102 at or near a first end 104, an elongated member 106 at a midsection 108, and a substrate 110 at or near a second end 112. The substrate 110 is disposed at an exterior surface of the stick 100. The substrate 110 includes a planar portion 114 at which a film of at least one detection element and at least one molecular receptor is supported. The at least one detection element and the at least one molecular receptor are coated onto the planar portion 114 of the substrate 110.

Preferably, the stick 100 is coated with or formed from an adsorptive material. Optionally, the substrate 110 has grooves in its external surface to increase a surface area at which molecular receptors and detection elements are supported.

Figure 6:
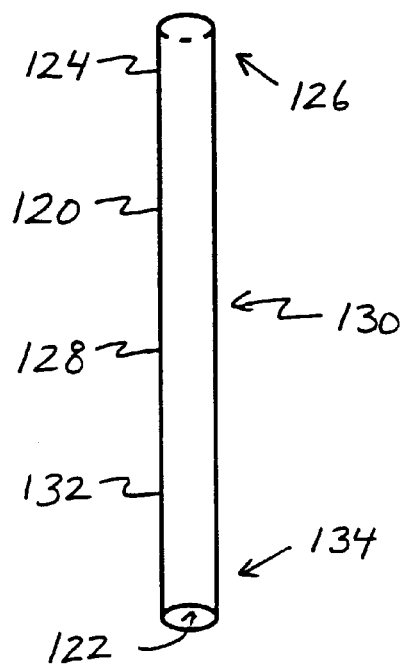
FIG. 6 illustrates a fifth embodiment of a molecular detection apparatus in accordance with the present invention.

FIG. 6 illustrates a fifth embodiment of a molecular detection apparatus in accordance with the present invention. The molecular detection apparatus includes a unitary member having the form of a stick 120 with a hollow portion 122. As illustrated, the hollow portion 122 can extend throughout the length of the stick 120. Additionally, either or both of the ends of the stick 120 can be sealed. The stick 120 can be formed of materials including but not limited to paper, plastic, wood, and glass. If desired, the stick 120 can be telescoping to have a smaller footprint in storage.

The stick 120 provides a grasping member 124 at or near a first end 126, an elongated member 128 at a midsection 130, and a substrate 132 at or near a second end 134. The substrate 132 can be disposed at an exterior surface, an interior surface, or both surfaces of the stick 120. At least one detection element and at least one molecular receptor are supported by a portion of the substrate 132.

Figure 7:
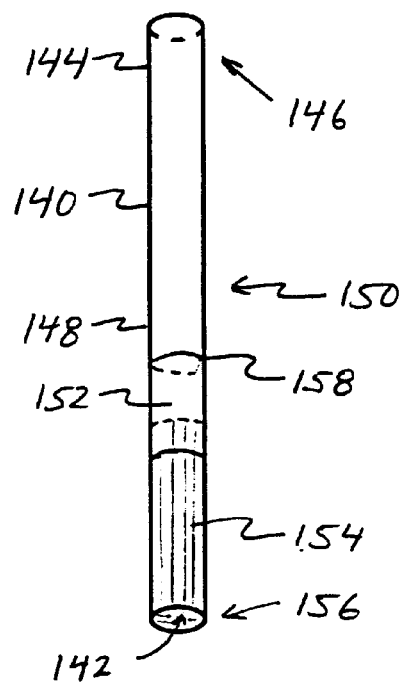
FIG. 7 illustrates a sixth embodiment of a molecular detection apparatus in accordance with the present invention.

FIG. 7 illustrates a sixth embodiment of a molecular detection apparatus in accordance with the present invention. The molecular detection apparatus includes a unitary member having the form of a stick 140 with a hollow portion 142. It is preferred that the stick 140 be formed of a transparent or a translucent material such as plastic or glass. The stick 140 provides a grasping member 144 at or near a first end 146, an elongated member 148 at a midsection 150, and a substrate 152 disposed within the hollow portion 142. If desired, the stick 140 can be telescoping to have a smaller footprint in storage.

A film of at least one detection element and at least one molecular receptor can be supported by the substrate 152. In this case, the detection element is positioned to be viewable from a location exterior to the stick 140. A wick 154 is disposed within the hollow portion 142 at or near a second end 156 of the stick 140. By capillary action, the wick 154 communicates a sample of a fluid from the second end 156 to the substrate 152. Molecules in the sample specific to the molecular receptor cause a visual indication in the detection element. The visual indication may be viewed through the stick 140 by an individual.

Alternatively, a solution of liposomes having the at least one detection element and the at least one molecular receptor can be disposed within the hollow portion 142. The solution can be contained anywhere from the first end 146 to the midsection 150. A breakable seal 158 contains the solution within the hollow portion 142. Once the wick 154 receives a sample of a fluid from the second end 156, the seal 158 can be broken to allow interaction between the sample and the solution. The seal 158 can be broken by squeezing or bending the portion of the stick 140 containing the solution. Molecules in the sample specific to the molecular receptor cause a visual indication in the detection element. The visual indication may be seen through the stick 140 by an individual.

The embodiments described with reference to FIGS. 2–7 are amenable for use in detecting predetermined molecules in a fluid. Here, an individual can grasp the molecular detection apparatus by the grasping member. While grasping the grasping member, the individual inserts a portion of the molecular detection apparatus into the fluid. Typically, the molecular detection apparatus is inserted so that the molecular receptors are immersed by the fluid. The individual can move, stir, or repeatedly dunk the molecular detection apparatus within the fluid to increase the likelihood of contacting the predetermined molecules. Thereafter, the individual removes the molecular detection apparatus from the fluid. The individual visually inspects the detection elements for the presence of the predetermined molecules in the fluid.

In one example, the fluid can include water in a container such as a cup or a bottle. An individual may wish to determine whether a pathogen is present in the water. Here, the individual can utilize a molecular detection apparatus having molecular receptors specific to the pathogen. The individual inserts the molecular detection apparatus into the container to visually detect the presence or absence of the pathogen.

The embodiment described with reference to FIG. 4 is advantageous in detecting molecules using a cap which seals a container of fluid. Shaking and mixing of the fluid during transportation of the container increases the likelihood of the molecules being adsorbed and detected by the molecular detection apparatus. A user can remove the cap from the container and inspect the detection elements to determine a condition of the fluid.

The embodiment described with reference to FIG. 7 is advantageous in that the molecular receptors and the detection elements come into contact only with a small sample of the fluid absorbed by the wick. Hence, the molecular receptors and the detection elements do not contact a portion of the fluid which is to be consumed.

Figure 8:
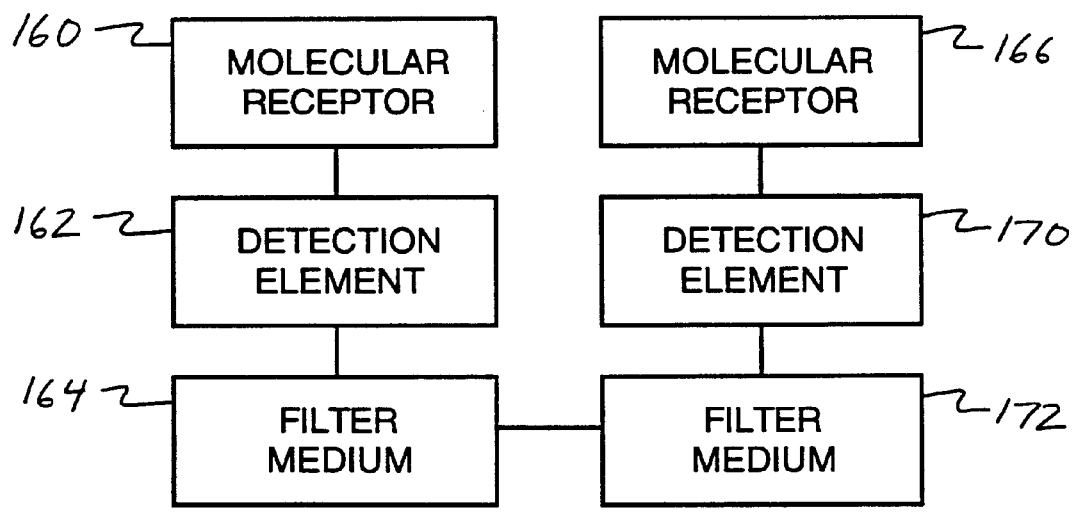
FIG. 8 is a block diagram that illustrates another embodiment of a molecular detection apparatus in accordance with the present invention.
Figure 4:
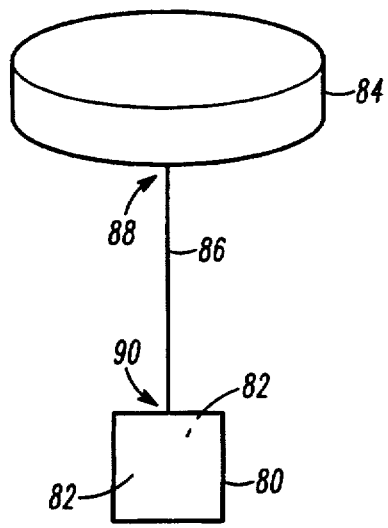
Figure 5:
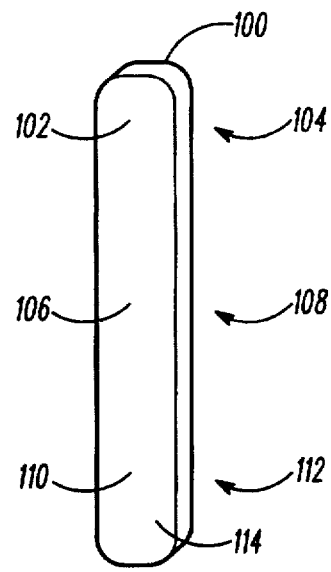
Figure 6:
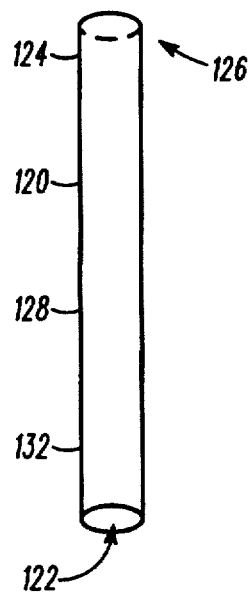
Figure 7:
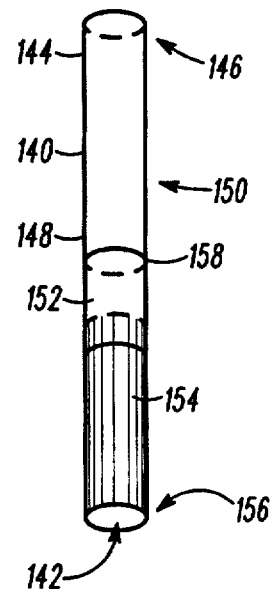
Figure 8:
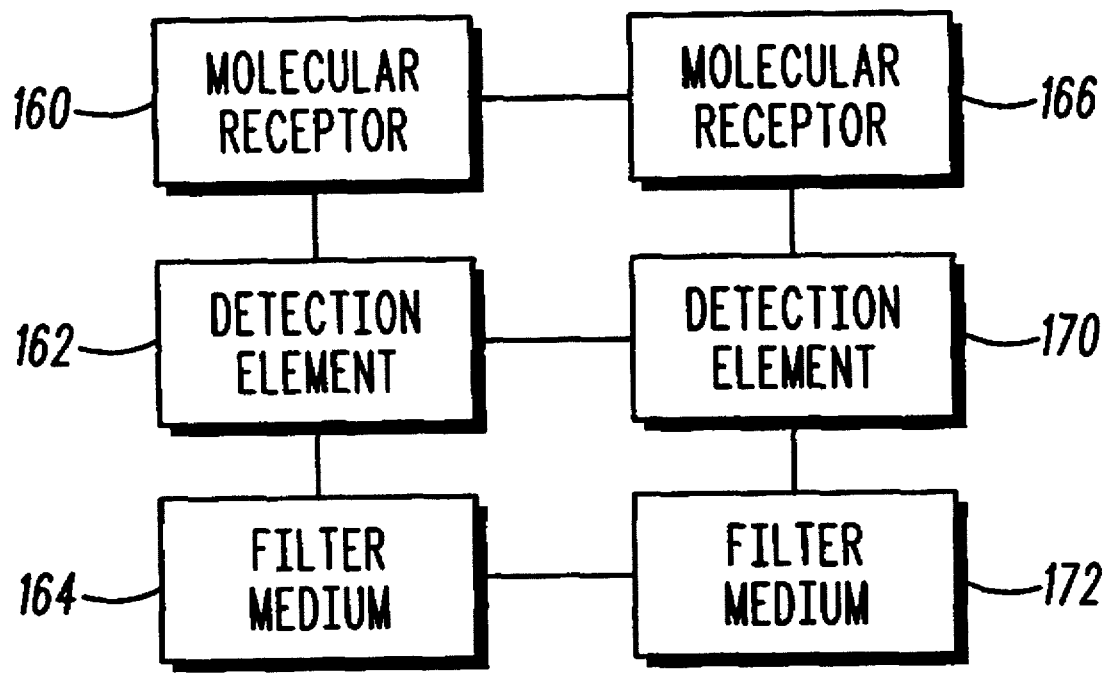

FIG. 8 is a block diagram of another embodiment of a molecular detection apparatus. The molecular detection apparatus comprises a first molecular receptor 160, a first detection element 162 responsive to the first molecular receptor 160, and a first filter medium 164 associated with the first detection element 162. The molecular detection apparatus further comprises a second molecular receptor 166, a second detection element 170 responsive to the second molecular receptor 166, and a second filter medium 172 associated with the first filter medium 164. The second filter medium 172 can be coupled to or attached to the first filter medium 164 to form a filter having a larger area.

The first molecular receptor 160 is utilized to detect a first type of molecule, and the second molecular receptor 166 is utilized to detect a second type of molecule. The first type of molecule differs from the second type of molecule. In general, the molecular detection apparatus can include any plurality of molecular receptors, detection elements, and filter media to detect any plurality of different molecules.

The molecular detection apparatus is utilized to detect predetermined molecules in a fluid which communicates therethrough. For example, a liquid such as water can be passed through the molecular detection apparatus to detect pathogens therein. The filter media are sized to accommodate a desired quantity of fluid. For example, the filter media can be sized for personal quantities of water, or for up to hundreds of liters and beyond.

If desired, a characteristic of the first filter medium 164 can differ from the second filter medium 172 so that a different amount of fluid is exposed to each. For example, the first filter medium can have a different porosity than the second filter medium, a different thickness than the second filter medium, and/or a different area than the second filter medium. By varying amounts of fluid exposed to different filter medium (and hence to different molecular receptors), more fluid can be sampled to detect rarer molecules than for more common molecules.

Thus, there has been described herein several embodiments including preferred embodiments of a molecular detection apparatus.

Because the various embodiments of the present invention utilize an elongated member to couple a grasping member to a molecular sensor, they provide a significant improvement in facilitating ease of use of an apparatus to detect predetermined molecules in a fluid.

Additionally, the various embodiments of the present invention pattern a plurality of detection elements in the form of an image to better communicate a condition of a fluid to a user.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A molecular detection apparatus comprising:
    an elongate member having a hollow portion and an end;
    a molecular receptor disposed within the hollow portion;
    a visual detection element responsive to the molecular receptor, the visual detection element viewable through the elongate member;
    a wick disposed within the hollow portion, at least a portion of the wick disposed between the molecular receptor and the end of the elongate member; and
    a breakable seal which separates the molecular receptor from the wick.

2. The molecular detection apparatus of claim 1 wherein the molecular receptor and the visual detection element are included in a solution of liposomes.

3. The molecular detection apparatus of claim 1 wherein the molecular receptor comprises a ligand.

4. The molecular detection apparatus of claim 1 wherein the visual detection element comprises a colorimetric detection element.

5. A molecular detection apparatus comprising:
    an extendible, elongate member having a hollow portion and an end;
    a molecular receptor disposed within the hollow portion;
    a visual detection element responsive to the molecular receptor, the visual detection element viewable through the elongate member; and
    a wick disposed within the hollow portion, at least a portion of the wick disposed between the molecular receptor and the end of the elongate member.

6. The molecular detection apparatus of claim 5 wherein the elongate member is telescoping.

7. The molecular detection apparatus of claim 5 wherein the molecular receptor and the visual detection element are included in a solution of liposomes.

8. The molecular detection apparatus of claim 5 wherein the molecular receptor comprises a ligand.

9. The molecular detection apparatus of claim 5 wherein the visual detection element comprises a colorimetric detection element.

* * * * *

UNITED STATES PATENT AND TRADEMARK OFFICE
CERTIFICATE OF CORRECTION

| | |
|---|---|
| PATENT NO. | : 5,948,694 |
| DATED | : September 7, 1999 |
| INVENTOR(S) | : Reber et al. |

It is certified that error appears in the above-identified patent and that said Letters Patent is hereby corrected as shown below:

In the Drawings
Please replace FIGS. 1-8 with the FIGS. 1-8, as shown on the attached.

Signed and Sealed this

Twenty-third Day of October, 2001

*Attest:*

NICHOLAS P. GODICI
*Attesting Officer*     *Acting Director of the United States Patent and Trademark Office*

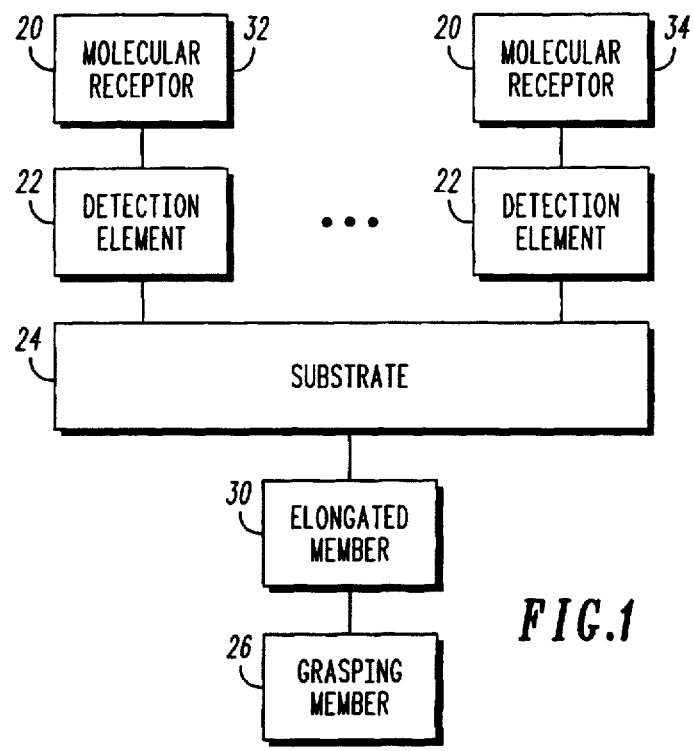
*FIG.1*
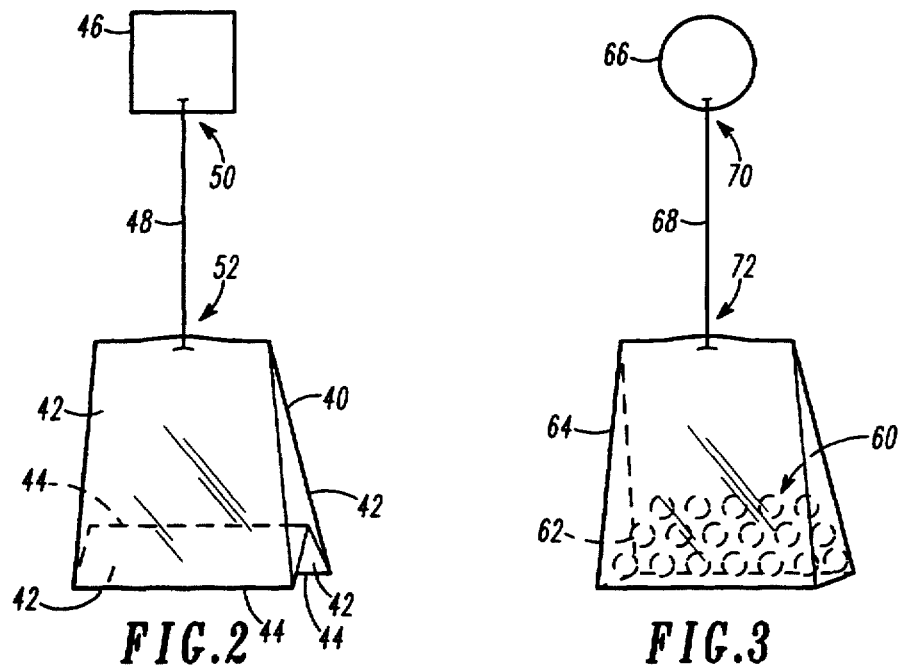
*FIG.2*  *FIG.3*